United States Patent
McCrory et al.

(10) Patent No.: US 10,451,580 B2
(45) Date of Patent: Oct. 22, 2019

(54) ROTATING DISK ELECTRODE CELL

(71) Applicant: California Institute of Technology, Pasadena, CA (US)

(72) Inventors: Charles McCrory, Ypsilanti, MI (US);
Suho Jung, Los Angeles, CA (US);
Ryan John-Robert Jones, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 186 days.

(21) Appl. No.: 15/133,954

(22) Filed: Apr. 20, 2016

(65) Prior Publication Data

US 2016/0313274 A1    Oct. 27, 2016

Related U.S. Application Data

(60) Provisional application No. 62/152,284, filed on Apr. 24, 2015.

(51) Int. Cl.
*G01N 27/403* (2006.01)
*C25B 9/12* (2006.01)
*G01N 27/30* (2006.01)

(52) U.S. Cl.
CPC .......... *G01N 27/403* (2013.01); *C25B 9/125* (2013.01); *G01N 27/308* (2013.01)

(58) Field of Classification Search
None
See application file for complete search history.

(56) References Cited

U.S. PATENT DOCUMENTS

| | | | | |
|---|---|---|---|---|
| 4,252,617 A | * | 2/1981 | Heusler | G01N 27/305 204/400 |
| 6,621,263 B2 | * | 9/2003 | Al-Janabi | G01N 17/02 324/200 |
| 2004/0007539 A1 | * | 1/2004 | Denes | C02F 1/4608 210/748.18 |
| 2013/0264222 A1 | * | 10/2013 | Bae | G01N 27/4166 205/782 |
| 2014/0004474 A1 | * | 1/2014 | Wang | H01M 4/8828 432/201 |

OTHER PUBLICATIONS

Gabe et al. (J. Appl. Electrochem, 13, 1983, 3-22).*
Pine (Modulated Speed Rotator (MSR) User Guide, published 2013, only a relevant portion of the text is included).*

* cited by examiner

*Primary Examiner* — Gurpreet Kaur
*Assistant Examiner* — Steven E Rosenwald
(74) *Attorney, Agent, or Firm* — Gavrilovich, Dodd & Lindsey LLP

(57) ABSTRACT

A rotating disk electrode cell has a housing with a reservoir configured to receive a sample for an electrochemical experiment. A shaft is positioned in the housing such that the shaft is free to rotate around the longitudinal axis of the shaft and such that both ends of the shaft are located inside of the housing.

20 Claims, 6 Drawing Sheets

ROTATING DISK ELECTRODE CELL

CROSS REFERENCE TO RELATED APPLICATIONS

This application claims the benefit of U.S. Provisional Patent Application Ser. No. 62/152,284, filed on Apr. 24, 2015, and incorporated herein in its entirety.

STATEMENT REGARDING FEDERALLY SPONSORED RESEARCH

This invention was made with government support under Grant No. DE-SC0004993/T-107914 awarded by the Department of Energy. The government has certain rights in the invention.

FIELD OF THE INVENTION

The present invention relates to electrochemistry, and more particularly, to a rotating disk electrode cell.

BACKGROUND

Experiments performed with rotating disk electrodes or rotating ring-disk electrodes often make use of gaseous reactants and/or produce gaseous products. Since it is often desirable to accurately quantify the amount of these reactants and/or products, there is a need for a gas-tight rotating disk electrode cell.

SUMMARY

A rotating disk electrode cell has a housing with a reservoir configured to receive a sample for an electrochemical experiment. A shaft is positioned in the housing such that the shaft is free to rotate around the longitudinal axis of the shaft and such that both ends of the shaft are located inside of the housing.

Another embodiment of the cell has a housing with a reservoir configured to receive a sample for an electrochemical experiment. A shaft is positioned in the housing with the shaft being free to rotate around the longitudinal axis of the shaft. One or more electrical brushes contact the shaft and are positioned inside of the housing.

Another embodiment of a rotating disk electrode cell includes a reservoir cover that holds a shaft such that the shaft is free to rotate around a longitudinal axis of the shaft without the shaft extending through the reservoir cover.

Yet another embodiment of a rotating disk electrode cell includes a reservoir cover that holds a shaft such that the shaft can rotate around a longitudinal axis of the shaft. One or more electrical brushes make contact with the shaft and are positioned inside of the cover.

BRIEF DESCRIPTION OF THE FIGURES

FIG. 1B is a bottomview of the rotating electrode assembly.

FIG. 1C is a cross section of the rotating electrode assembly shown in FIG. 1B taken through the longitudinal axis of the rotating electrode assembly.

FIG. 1D is a bottomview of the rotating electrode assembly.

FIG. 1E is a cross section of the rotating electrode assembly taken through the longitudinal axis of the rotating electrode assembly.

FIG. 2A is a perspective view of the cell. The cell has a housing that includes a base, a sub-reservoir cover, and an assembly cover that holds the rotating electrode assembly.

FIG. 2B is a cross section of the assembly cover used in the cell shown in FIG. 2A.

FIG. 2C is a cross section of the sub-reservoir cover used in the cell shown in FIG. 2A.

DESCRIPTION

As used herein and in the appended claims, the singular forms "a," "and," and the include plural referents unless the context clearly dictates otherwise. Thus, for example, reference to "a parasite" includes a plurality of such parasites and reference to "the enzyme" includes reference to one or more enzymes known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Any publications discussed above and throughout the text are provided solely for their disclosure prior to the filing date of the present application. Nothing herein is to be construed as an admission that the inventors are not entitled to antedate such disclosure by virtue of prior disclosure.

A rotating disk electrode cell includes a housing that has a reservoir for holding the sample for a rotating disk electrode experiment and/or a rotating ring-disk electrode experiment. The cell includes a working electrode mounted on a follower shaft that is positioned entirely within the housing with the follower shaft being free to rotate within the housing. The follower shaft is magnetically coupled to a drive shaft across the housing. The drive shaft can be rotated. The rotation of the drive shaft causes the follower shaft to rotate as a result of the magnetic coupling between the drive shaft and the follower shaft. Accordingly, an external source is employed to rotate the drive shaft during the experiments. The rotation of the drive shaft during these experiments provides the desired rotation of the follower shaft and accordingly the desired rotation of the working electrode. The desired rotation can be achieved without either shaft extending through the housing. Since neither shaft penetrates the housing, the housing can be air-tight or gas-tight.

Figure 1A:
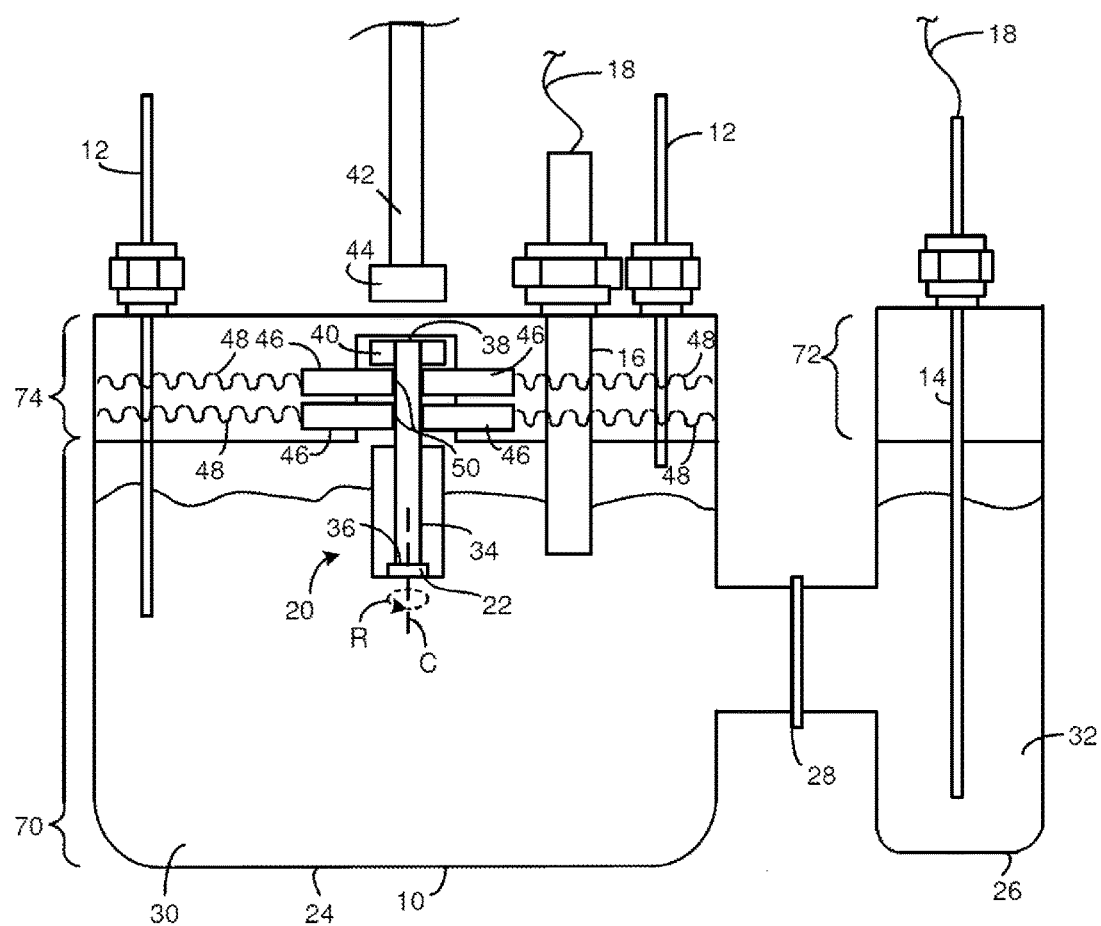
FIG. 1A is a schematic of a cell that can be operated as a rotating disk electrode cell and/or a rotating ring-disk electrode cell. The cell includes a rotating electrode assembly that includes a working electrode.

FIG. 1A is a schematic of a rotating disk electrode cell. The cell has a housing 10 that includes a reservoir. During operation of the cell, a sample to be tested can be located in the reservoir. The sample can be a fluid, liquid, gas, or a combination. For instance, the sample can include a gas over a liquid. In some instances, the cell is constructed so as to be impermeable to the atmosphere in which the cell is positioned. For instance, the cell can be air-tight.

The cell can optionally include one or more material conduits 12 that provide a conduit into the reservoir and/or out of the reservoir. A material conduit 12 can be employed to input one or more materials into the reservoir from a location outside of the reservoir and/or to remove one or more materials from within the reservoir to a location outside of the reservoir. The materials can include, consist of, or consist essentially of reactants for and/or products of chemical reactions that occur during operation of the cell. In one example, one of the material conduits 12 is employed to deliver a gaseous reactant directly into the liquid portion of the sample and another material conduit 12 is used to withdraw the liquid portion of the sample. An example of a suitable gaseous reactant includes, but is not limited to, $CO_2$, $H_2$, $O_2$, and $N_2$. In some instances, the one or more material conduits 12 are used to operate the cell as a flow reactor and/or continuous reactor during electrochemical testing of the sample. The one or more material conduits 12 are optional. For instance, the cell can exclude material conduits 12. In some instances where the cell excludes material conduits 12, the cell is operated as a batch reactor during electrochemical testing of the sample.

When the cell includes one or more material conduits 12 that extend through the housing 10, the connection between the housing 10 and each of the material conduits 12 can be constructed so as to provide a gas-tight or airtight seal between the material conduit 12 and the housing 10 as is well known in the chemistry arts.

The cell includes one or more electrodes positioned in the reservoir so the one or more electrodes are exposed to the sample. In some instances, at least a portion of each of the electrodes is in direct physical contact with the sample. In some instances, one or more of the electrodes extends through the housing 10. For instance, FIG. 1A illustrates a counter electrode 14 and a reference electrode 16 extending through the housing 10. Suitable reference electrodes 16 include, but are not limited to, Ag/AgCl, Hg/HgCl, and Hg/HgO. Suitable counter electrodes 14 include, but are not limited to, graphite, Pt, and Au.

When the cell includes one or more electrodes that extend through the housing 10, the connection between the housing 10 and the electrode can be constructed so as to provide a gas-tight or airtight seal between the electrode and the housing 10 as is well known in the chemistry arts.

The one or more electrodes can be in electrical communication with electronics that operate the cell. For instance, conductors such as wires 18 and/or electrical cables can provide electrical communication between an electrode and the electronics. As a result, the electronics can apply and/or measure the potential at the reference electrode and/or counter electrode and/or measure the level of electrical current through the reference electrode and/or counter electrode.

FIG. 1A illustrates the conductors positioned outside of the reservoir and the electrodes extending across the housing 10; however, one or more of the electrodes can be positioned entirely within the reservoir and the associated conductors can extend across the housing 10. When a conductor extends across the housing 10, the connection between the conductor and the housing 10 can be constructed so as to provide an impermeable or airtight seal between the conductor and the housing 10.

The cell also includes a rotating electrode assembly 20 that includes a working electrode 22. When the cell includes a counter electrode 14, the counter electrode 14 can be chemically isolated from the working electrode 22. When the electrodes include a counter electrode 14 and a reference electrode 16, the counter electrode 14 can be chemically isolated from the working electrode 22 and/or the reference electrode 16. For instance, the housing 10 can define two or more sub-reservoirs or can define only a single reservoir. The housing 10 illustrated in FIG. 1A defines a first sub-reservoir 24 and a second sub-reservoir 26. A composition isolator 28 can span the space between sub-reservoirs. FIG. 1A shows a composition isolator 28 spanning the space between the sub-reservoirs so as to separate a first portion 30 of the sample from a second portion 32 of the sample. One of the sub-reservoirs includes the first portion 30 of the sample and the assembly 20 while the second sub-reservoir includes the second portion 32 of the sample and the counter electrode 14. As a result, the working electrode 22 and/or reference electrode 16 are exposed to the first portion 30 of the sample and the counter electrode 14 is exposed to the second portion 32 of the sample.

The composition isolator 28 can be selected to stop a component formed at the counter electrode 14 from traveling through the sample to the working electrode 22. For instance, when reduction occurs at the working electrode 22, oxygen is often formed at the counter electrode 14. The composition isolator 28 can be configured to prevent the passage of the oxygen through the composition isolator 28. Accordingly, in order to permit charge balancing within the reservoir, the composition isolator 28 can be selected to permit the passage of ions through the composition isolator 28 without allowing bulk mixing of the first portion 30 of the sample and the second portion 32 of the sample. Suitable composition isolators 28 include, but are not limited to, frits such as glass frits, a salt bridge, and ionomer membranes such as semipermeable membranes, and ion exchange membranes such as anion exchange membranes and cation exchange membranes.

The rotating electrode assembly 20 includes a follower shaft 36 that has a first end 38 and a second end. The working electrode 22 is attached to the first end 38 of the follower shaft 36. The follower shaft 36 is located within the reservoir. For instance, the first end 38 of the follower shaft 36 and the second end of the follower shaft 36 are both positioned inside of the housing 10. The second end of the follower shaft 36 is between the first end of the shaft and the housing 10. For instance, the housing extends over the second end of the follower shaft 36. A follower magnet 40 is immobilized on the follower shaft 36. Suitable methods of immobilizing the follower magnet 40 on the follower shaft 36 include, but are not limited to, side set screws, threads, and gluing. In some instances, the follower magnet 40 surrounds the follower shaft 36. The follower shaft 36 is configured to rotate around the central axis labeled C in FIG. 1A. In some instances, the working electrode 22 is positioned such that the rotation of the follower shaft 36 causes the working electrode 22 to rotate around the central axis labeled C in FIG. 1A.

A drive shaft 42 is located outside of the reservoir and is magnetically coupled to the follower shaft 36. A drive magnet 44 is immobilized on the drive shaft 42. Suitable methods of immobilizing the drive magnet 44 on the drive shaft 42 include, but are not limited to, set screws, adapters, threads, and attaching with glues, epoxies or adhesives. The drive magnet 44 and the follower magnet 40 are magnetically coupled across the housing 10. The magnetic coupling of the drive magnet 44 and the follower magnet 40 provides magnetic coupling of the follower shaft 36 and the drive shaft 42. The drive shaft 42 is configured to rotate around a central axis of the drive shaft 42. The magnetic coupling of the drive shaft 42 and the follower shaft 36 causes the follower shaft 36 to rotate in response to rotation of the drive shaft 42 by an external power source. In some instances, the drive shaft 42 is aligned with the follower shaft 36 such that the drive shaft 42 and follower shaft 36 both rotate around the central axis labeled C in FIG. 1A. The rotation of the follower shaft 36 within the reservoir provides rotation of the working electrode 22 as illustrated by the arrow labeled R in FIG. 1A.

The cell includes electrical brushes 46 that each contacts the rotating electrode assembly 20. FIG. 1A illustrates a lower set of brushes 46 and an upper set of brushes 46. Urging devices 48 can place urge or push the brushes 46 toward the rotating electrode assembly 20. For instance, FIG. 1A illustrates compressed springs that push the brushes 46 toward the rotating electrode assembly 20. Other examples of suitable urging devices 48 include, but are not limited to, metal rods, pogo pins, and metal needles. Although not evident from FIG. 1A, the rotating electrode assembly 20 includes one or more electrical contacts 50 and each of the brush 46 is urged into contact with one of the electrical contacts 50. The details of the electrical contacts 50 are not illustrated in the assembly 20 of FIG. 1A in order to simplify the illustration, however, the assembly 20 construction is detailed below. The pushing of the brushes 46 against the rotating electrode assembly 20 permits the contact between the brush 46 and the electrical contact 50 even while the rotating electrode assembly 20 is rotating. Suitable brushes 46 include, but are not limited to, carbon brushes, carbon-silver brushes, carbon-copper brushes, and carbon-$MoS_2$ brushes.

The rotating electrode assembly 20 includes one or more electrodes. For instance, the rotating electrode assembly 20 can include a working electrode 22 and/or a ring electrode 60. The rotating electrode assembly 20 is constructed so as to provide electrical communication between the electrodes and the electrical contacts 50. For instance, one or more of the electrodes included in the assembly 20 can each be in electrical communication with one of the electrical contacts 50. Since the brushes 46 are urged into contact with the electrical contacts 50 during rotation of the rotating electrode assembly 20, the rotating electrode assembly 20 provides electrical communication between the brushes 46 and the electrodes during rotation of the rotating electrode assembly 20. The brushes 46 can be in electrical communication with the electronics through the use of wires, cables, or other conductors. Since the brushes 46 are in electrical communication with the working electrode 22, the electronics can set the potential of the electrodes during the operation of the assembly 20.

Figure 1B:
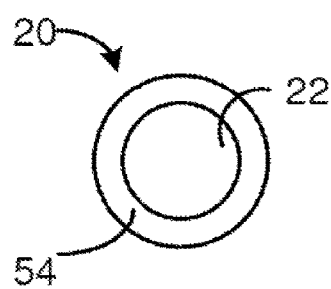
FIG. 1B and FIG. 1C illustrate an example of a suitable rotating electrode assembly.
Figure 1C:
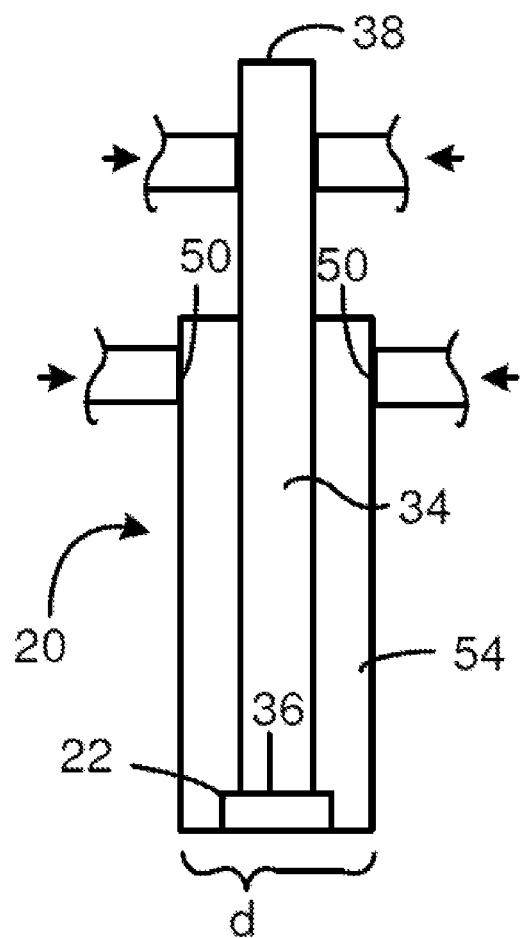

FIG. 1B and FIG. 1C illustrate an example of a suitable rotating electrode assembly 20. FIG. 1B is a bottomview of the assembly 20 and FIG. 1C is a cross section of the assembly 20 taken through the longitudinal axis of the assembly 20. The assembly 20 includes a working electrode 22 in contact with the follower shaft 36. A shroud 54 is positioned over the lateral side and upper surface of the working electrode 22 and also over a portion of the follower shaft 36. The shroud 54 is generally constructed of an electrically insulating material such as Teflon, polyetheretherketone (PEEK), or polyetheretherketone (Kel-F). The functional surface of the shroud 54 has a diameter labeled d in FIG. 1C. The diameter of the functional surface is generally sufficient to achieve the desired diffusion layer during operation of the assembly 20. A suitable diameter includes diameters greater than 13 mm, 14 mm, or 15 mm and/or less than 20 mm, 21 mm, or 22 mm. A suitable diameter for the working electrode 22 includes diameters greater than 3 mm, 4 mm, or 5 mm and/or less than 12 mm, 13 mm, or 14 mm.

As is evident in FIG. 1C, the upper set of brushes 46 are pushed against the lateral side of the follower shaft 36. The follower shaft 36 contacts the working electrode 22 or is attached to the working electrode 22 by an electrically conducting connection. Additionally, the follower shaft 36 can be electrically conducting. As a result, the follower shaft 36 provides electrical communication between the upper set of brushes 46 and the working electrode 22. In this instance, the surface of the follower shaft 36 serves as the electrical contacts 50 for the brushes 46. Since the surface of the follower shaft 36 extends all of the way around perimeter of the shaft, the contact between the electrical contacts 50 and the brushes 46 is maintained as the assembly 20 rotates.

The lower set of brushes 46 are in contact with the shroud 54 and do not contact the follower shaft 36. Since the shroud 54 is electrically insulating, in this embodiment, the lower set of brushes 46 are not in electrical communication with an electrode included on the assembly 20.

The brushes 46 can be in electrical communication with the electronics through the use of wires, cables, or other conductors. Since the brushes 46 are in electrical communication with the working electrode 22, the electronics can set the potential of the working electrode 22 during the operation of the assembly 20. For instance, the electronics can set the potential of the working electrode 22 during the rotation of the assembly 20.

Figure 1D:
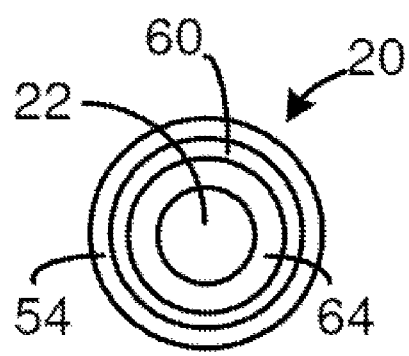
FIG. 1D and FIG. 1E illustrate another example of a rotating electrode assembly.
Figure 1E:
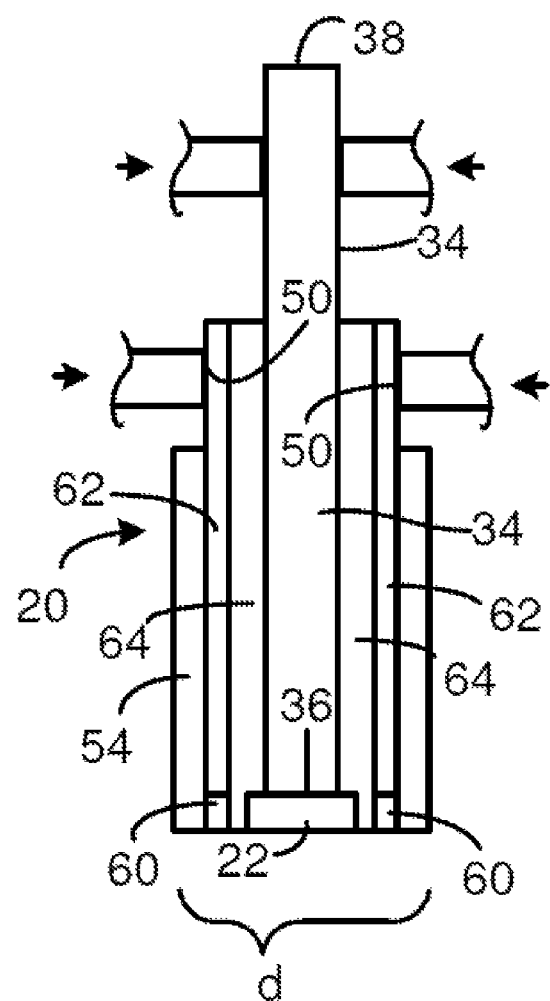

FIG. 1D and FIG. 1E illustrate another example of a rotating electrode assembly 20 that is suitable for use as a rotating ring-disk electrode. FIG. 1D is a bottomview of the assembly 20 and FIG. 1E is a cross section of the assembly 20 taken through the longitudinal axis of the assembly 20. The assembly 20 includes a working electrode 22 in contact with the follower shaft 36 and a ring electrode 60 in contact with a ring conductor 62. In some instances, the ring conductor 62 surrounds the follower shaft 36. As a result, the ring conductor 62 can be constructed as a ring or cylinder. An insulator 64 is between the working electrode 22 and the ring electrode 60. Additionally, the insulator 64 is positioned between the follower shaft 36 and the ring conductor 62. As a result, the insulator 64 serves to electrically insulate the ring electrode 60 from the working electrode 22. Suitable materials for the ring electrode 60 include, but are not limited to, Au, Pt, and Ag. Suitable materials for the working electrode 22 include, but are not limited to, Cu, Ni, and Co. Suitable materials for the ring conductor 62 conductor include, but are not limited to, Cu, Al, and Pt.

A shroud 54 is positioned over lateral side of the ring electrode 60 and also over a portion of the electrical insulator 64. The shroud 54 is generally constructed of an electrically insulating material such as Teflon, polyetheretherketone (PEEK), or Polyetheretherketone (Kel-F). The insulator 64 can be constructed of the same material as the shroud 54 or from a different material. The functional surface of the shroud 54 has a diameter labeled d in FIG. 1E. The diameter of the functional surface is generally sufficient to achieve the desired diffusion layer during operation of the assembly 20. A suitable diameter, d, includes diameters greater than 13 mm, 14 mm, or 15 mm and/or less than 20 mm, 21 mm, or 22 mm. A suitable diameter for the working electrode 22 includes diameters greater than 3 mm, 4 mm, or 5 mm and/or less than 12 mm, 13 mm, or 14 mm. A suitable outer diameter for the ring electrode 60 includes diameters greater than 5 mm, 6 mm, or 7 mm and/or less than 14 mm, 15 mm, or 16 mm.

As is evident in FIG. 1E, the upper set of brushes 46 are pushed into contact with the lateral side of the follower shaft 36. The follower shaft 36 contacts the working electrode 22 or is attached to the working electrode 22 by an electrically conducting connection. Additionally, the follower shaft 36 can be electrically conducting. As a result, the follower shaft 36 provides electrical communication between the upper set of brushes 46 and the working electrode 22. In this instance, the surface of the follower shaft 36 serves as the electrical contacts 50 for the brushes 46. Since the surface of the follower shaft 36 extends all of the way around perimeter of the shaft, the contact between the electrical contacts 50 and the brushes 46 is maintained as the assembly 20 rotates.

The lower set of brushes 46 are in pushed into contact with the lateral side of the ring conductor 62. The ring conductor 62 contacts the ring electrode 60 or is attached to the ring electrode 60 by an electrically conducting connection. Since the ring conductor 62 is electrically conducting, the ring conductor 62 provides electrical communication between the lower set of brushes 46 and the working electrode 22. In this instance, the surface of the ring conductor 62 serves as the electrical contacts 50 for the brushes 46. Since the surface of the ring conductor 62 can extend all of the way around perimeter of the ring conductor 62, the contact between the ring conductor 62 and the brushes 46 is maintained as the assembly 20 rotates.

The brushes 46 can be in electrical communication with the electronics through the use of wires, cables, or other conductors. Since one or more of the brushes 46 are in electrical communication with the working electrode 22, the electronics can apply the desired potential to the working electrode 22 during the operation of the assembly 20. The potential at the working electrode 22 can be constant or varied depending on the electrochemical experiment being performed. Similarly, the electronics can apply the desired potential to the ring electrode 60 during the operation of the assembly 20. The potential at the ring electrode 60 can be constant or varied depending on the electrochemical experiment being performed. Since the assembly 20 arranges the working electrode 22 and ring electrode 60 such that they are electrically insulated from one another, the electronics apply a different potential to the working electrode 22 and the ring electrode 60 or can apply the same potential to the working electrode 22 and the ring electrode 60. As a result, the cell can be a cell for a rotating ring-disk electrode.

When using the assembly 20 of FIG. 1A through FIG. 1C, the cell can be operated as a rotating disk electrode cell. However, when using the assembly 20 of FIG. 1A and FIG. 1D through FIG. 1E, the cell can be operated as a rotating ring-disk electrode cell. As a result, the same housing 10 can be used to perform either type of experiment.

The housing 10 can be constructed of a single piece or multiple pieces. The housing 10 illustrated in FIG. 1A includes a base 70, a sub-reservoir cover 72 that holds the counter electrode 14, and an assembly cover 74 that holds the assembly 20.

Figure 2A:
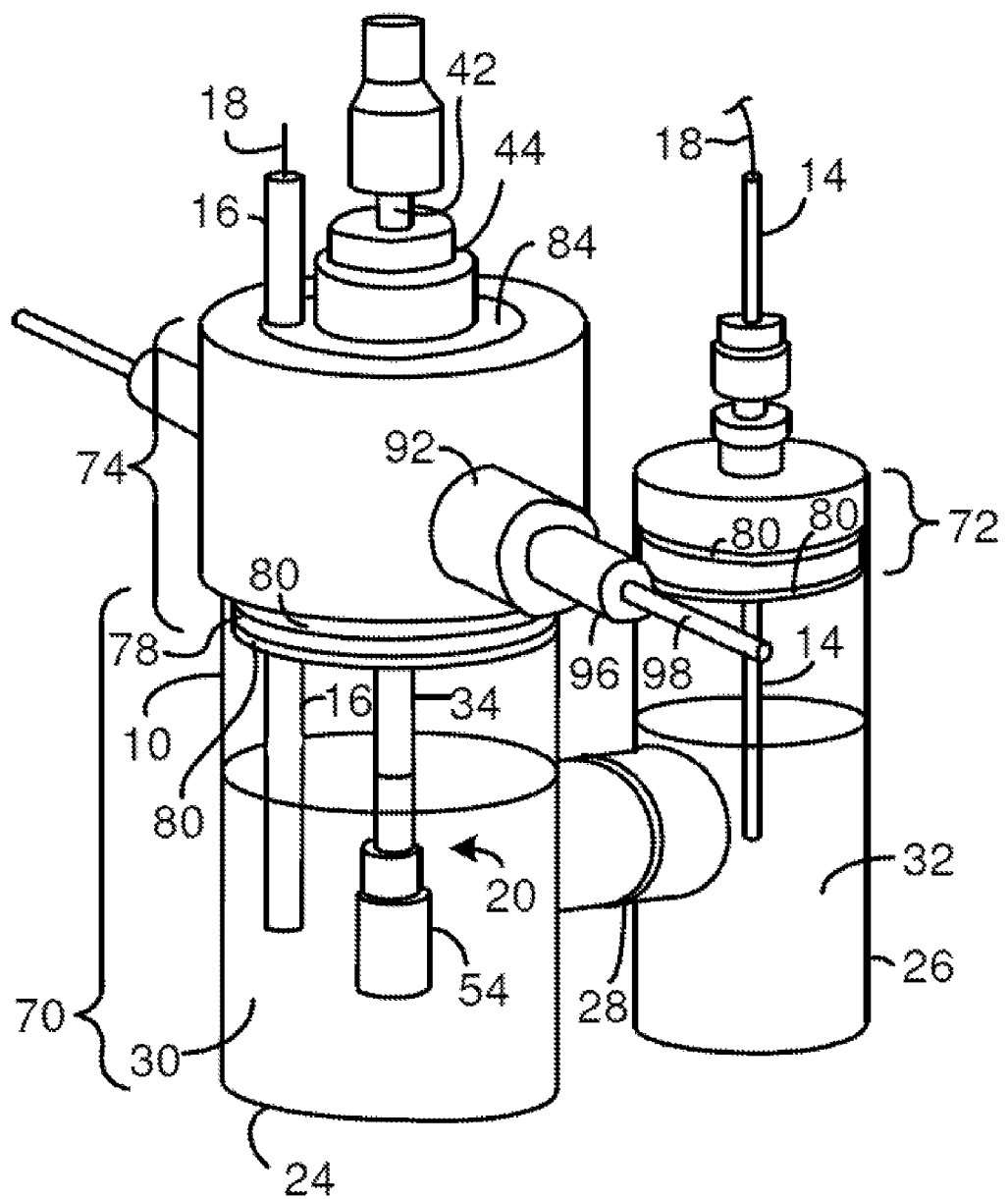
FIG. 2A through FIG. 2C illustrate an embodiment of a cell constructed according to FIG. 1A through FIG. 1E.
Figure 2B:
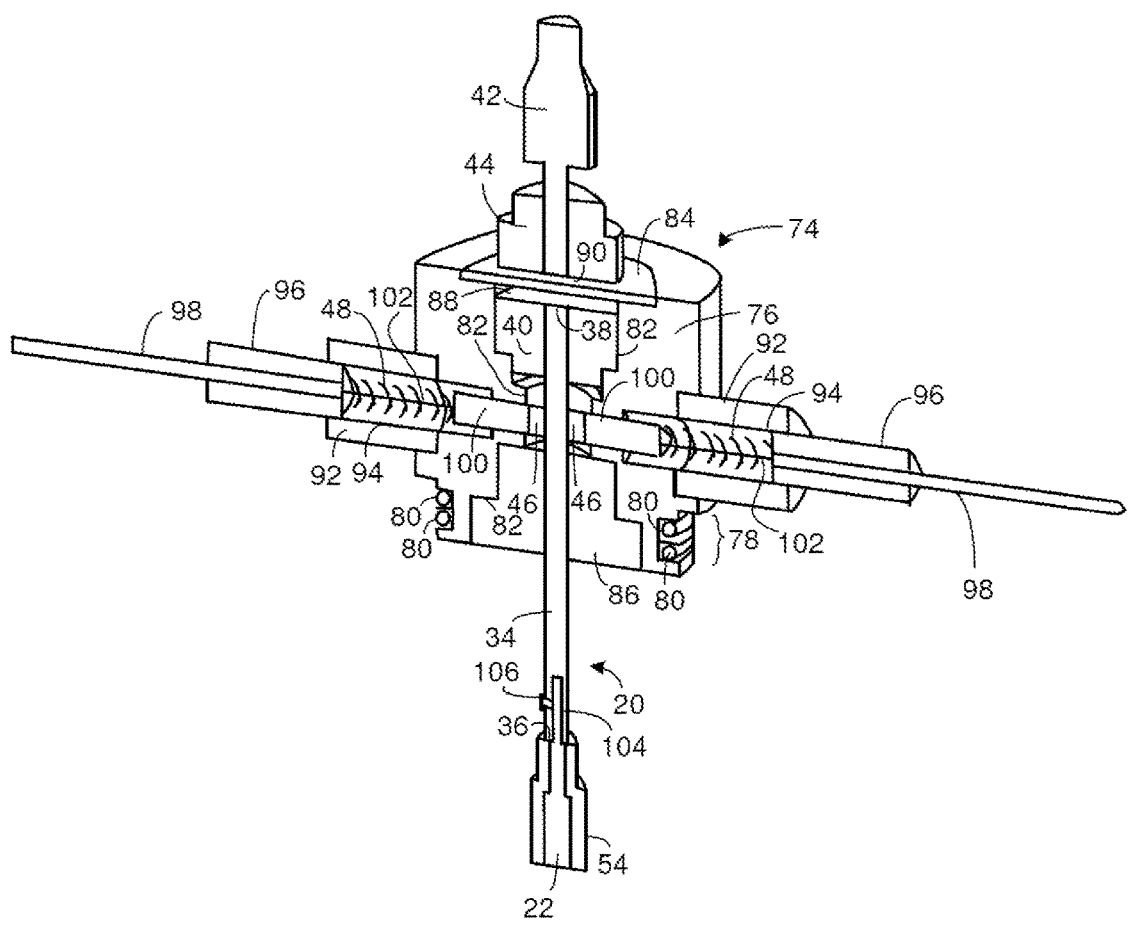
Figure 2C:
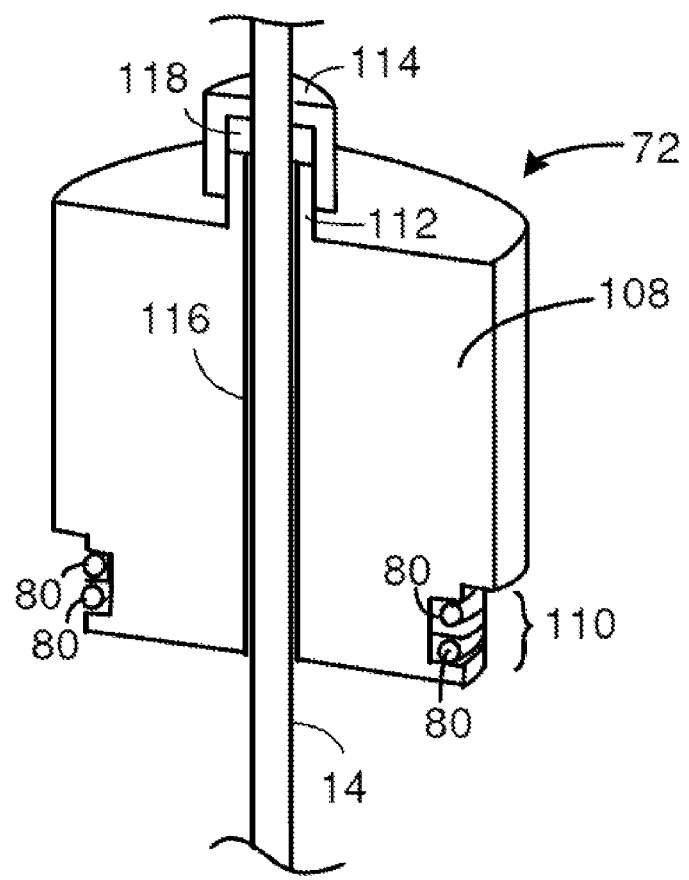

FIG. 2A through FIG. 2C illustrate an embodiment of a cell constructed according to FIG. 1A through FIG. 1E. FIG. 2A is a perspective view of the assembled cell. FIG. 2B is a cross section of the assembly cover 74 shown in FIG. 2A.

The cross section is taken through the longitudinal axis of the follower shaft 36. FIG. 2C is a cross section of the sub-reservoir cover 72 shown in FIG. 2A. The cross section is taken through the longitudinal axis of the counter electrode 14. The one or more material conduits 12 shown in FIG. 1A are not shown in the embodiment of FIG. 2A through FIG. 2B in order to simplify the illustration. However, when the cell includes one or more material conduits 12, one or more of the material conduits 12 can extend through the assembly cover 74 and/or through the sub-reservoir cover 72.

The assembly cover 74 includes a frame 76 that supports the various parts of the assembly cover 74. The frame 76 can be constructed of a single piece or multiple pieces. In some instances, the frame 76 is electrically insulating. Suitable materials for the frame 76 include, but are not limited to, Teflon, Plexiglass, PEEK, and Kel-F. The fame includes a coupling portion 78 that is received within the base 70. The coupling portion 78 can include one or more sealing mechanisms 80 that provide a seal between the coupling portion 78 and the base 70. For instance, FIG. 2A and FIG. 2B illustrate o-rings that surround the coupling portion 78 such that the o-rings are positioned between the housing 10 and the base 70 upon construction of the cell. Other examples of suitable sealing mechanisms 80 include, but are not limited to, Silicone o-ring, PTFE coated Silicone o-ring, and Viton.

A shaft passage 82 extends into or through the frame 76. The shaft passage 82 illustrated in FIG. 2B extends through the frame 76. The follower shaft 36 is received within the shaft passage 82. In FIG. 2B, a passage cover 84 is attached to the frame 76 extends across an upper opening of the shaft passage 82. Suitable passage covers 84 are "conductive" of magnetic flux. Examples of suitable materials for the passage cover 84 include, but are not limited to, Teflon, Plexiglass, and Kel-F. The passage cover 84 can be attached to the frame 76. In some instance, there connection of the passage cover 84 to the frame 76 is impermeable to gasses and/or is air tight in order to provide a reservoir that is sealed from the atmosphere in which the cell is positioned. For instance, a sealing mechanism such as a gasket or o-ring can be positioned between the passage cover 84 and the frame 76. Suitable methods for attached the passage cover 84 to the frame 76 include, but are not limited to, o-rings, threads, and attachment with adhesives such as glues, and epoxies. The use of a passage cover 84 that is separate from the frame 76 is not necessary as the frame 76 itself may terminate the shaft passage 82 and can accordingly serve as the shaft cover.

The shaft passage 82 includes a seat that receives a shaft holder 86. The shaft holder 86 can be immobilized relative to the shaft passage 82. Suitable methods for immobilizing the shaft holder 86 relative to the shaft passage 82 include, but are not limited to, ball-bearing, bushing, and roller-bearing. The follower shaft 36 extends through the shaft holder 86 such that the shaft holder 86 is located between the first end of the shaft holder 86 and the second end of the shaft holder 86. The shaft holder 86 is configured to permit rotation of the follower shaft 36 while preventing or reducing linear movement of the follower shaft 36. As a result, the shaft holder 86 permits rotation of the follower shaft 36 in the shaft passage 82. Examples of suitable shaft holders 86 include, but are not limited to, bearing assemblies.

The follower shaft 36 is received in the shaft passage 82 without extending through the shaft cover. Accordingly, the follower shaft 36 does not extend outside of the housing 10 for the cell. The follower shaft 36 is shown extending through the follower magnet 40, however, the follower shaft 36 can terminate within the follower magnet 40 such that a portion of the follower magnet 40 extends over the second end of the follower shaft 36. The second end of the follower shaft 36 and the follower magnet 40 are not immobilized relative to the shaft cover so as to permit the follower shaft 36 and follower magnet 40 to rotate within the shaft passage 82. For instance, the second end of the follower shaft 36 and the follower magnet 40 can be spaced apart from the shaft cover. As a result, a gap 88 can be located between the passage cover 84 and the follower magnet 40 and the second end of the follower shaft 36. A fluid within the shaft passage 82 can be within the gap 88. For instance, air can be located in the gap 88.

The drive shaft 42 is shown extending through the drive magnet 44, however, the drive shaft 42 can terminate within the drive magnet 44 such that a portion of the drive magnet 44 extends over the end of the drive shaft 42. The end of the drive shaft 42 and the drive magnet 44 are not immobilized relative to the shaft cover so as to permit rotation of the drive shaft 42. For instance, the end of the drive shaft 42 and the drive magnet 44 can be spaced apart from the shaft cover. As a result, a gap 90 can be located between the passage cover 84 and the drive magnet 44 and the drive shaft 42. The atmosphere in which the cell is positioned can be within the gap 90. For instance, a fluid such as air can be located in the gap 90. The drive shaft 42 is aligned with the follower shaft 36 such that the drive shaft 42 and follower shaft 36 both rotate around the same axis of substantially the same axis.

Brush passages extend from an external side of the frame 76 to the shaft passage 82. Arms 92 are received in the brush passages. A channel 94 extends through each arm 92 and is aligned with one of the brush passages. Suitable arms 92 include, but are not limited to, tubes, threaded rods, conduits, ferrules and cylinders. In some instances, the arms 92 are electrically insulating. Suitable materials for the arm 92 include, but are not limited to, Teflon, Plexiglass, and Kel-F. The arms 92 can be immobilized relative to the frame 76. Additionally, an impermeable and/or air tight seal can be formed between the arm 92 and the frame 76. Suitable methods for attaching the arm 92 and the frame 76 include, but are not limited to, threads, sealants, o-ring seals, and adhesives such as glues and epoxies.

A connector 96 is received within the channel 94 of each arm 92. An electrical conductor 98 extends through each of the connectors 96. In some instances, the connector 96 is constructed of an electrically insulating material. Suitable materials for the connector 96 include, but are not limited to, Teflon, Plexiglass, and Kel-F. There can be a gas-impermeable or air-tight seal between the connector 96 and the arm 92. For instance, a connector 96 can be received in the channel 94 of an arm 92 such that a seal is formed between the connector 96 and the channel 94 of the arm 92. Suitable methods of forming the seal between the connector 96 and the channel 94 include, but are not limited to, ferrule seals, Teflon tape seals, and thread seals. Suitable connectors include, but are not limited to, Swagelok fittings available from Swagelok located in Solon, Ohio, USA, NPT fittings available from Swagelok, Solon Ohio, USA, Ace threads available from ACE Glass, Vineland, N.J., USA, and IDEX fittings available from Oak Harbor, Wash., USA.

As noted above, a conductor 98 extends through each of the connectors 96. Suitable conductors 98 include, but are not limited to, wires and metal rods. The conductor 98 can be immobilized relative to the connector 96 such that a gas-impermeable or air-tight seal is formed between the connector 96 and the conductor 98. Suitable methods of forming the seal between the connector 96 and the conductor 98 include, but are not limited to, ferrules, o-ring sealing, and attachment with adhesives such as glues and epoxies. The conductors 98 can be in electrical communication with the electronics through the use of wires, cables and/or other conductors 98.

Brush holders 100 are positioned in the brush passages and each holds one of the brushes 46. In some instances, the brush holders 100 can be constructed of an electrically conducting material. Alternately, a brush 46 can extend through the brush holder 100 and the brush holder 100 can be electrically conducting or electrically insulating. Suitable materials for the brush holders 100 include, but are not limited to, Al, stainless steel, and brass. Springs are positioned in the brush passages and serve as the urging devices 48 that push the brushes 46 into contact with the follower shaft 36.

Secondary conductors 102 contact the conductors 98 and/or are attached to the conductors 98 by an electrically conducting connection. Additionally, the secondary conductors 102 contact the brush holders 100 and/or the brushes 46 and/or are attached to the brush holders 100 and/or the brushes 46 by an electrically conducting connection. As a result, electrical communication between the brushes 46 and the conductors 98 occurs through the secondary conductors. Suitable secondary conductors 102 include, but are not limited to, Cu, Al, and Ag.

The rotating electrode assembly 20 illustrated in FIG. 2B includes a working electrode 22 having a coupling portion 104 that extends out of the shroud 54. The follower shaft 36 includes a recess that receives coupling portion 104 of the working electrode 22. An attachment device such as a set screw 106 can be employed to secure the working electrode 22 and shroud 54 relative to the follower shaft 36. The optional use of one or more attachment devices allow the working electrode 22 to be optionally removed from the follower shaft. Similarly, when the rotating electrode assembly includes a ring electrode, the use of one or more attachment devices allow the working electrode 22 and ring electrode to be removed from the follower shaft.

For the purposes of illustration, the example cell of FIG. 2A and FIG. 2B is a rotating disk electrode cell. As a result, the assembly 20 includes a single electrode and the assembly cover 74 includes a single set of brushes 46. However, the cell can be converted to a rotating ring-disk electrode cell by inclusion of one or more additional sets of brushes 46 in the assembly cover 74 and the use of an assembly 20 that includes multiple electrodes that are each in electrical communication with one of the sets of brushes 46 as shown in FIG. 1D and FIG. 1E.

The sub-reservoir cover 72 includes a frame 108 that supports the various parts of the sub-reservoir cover 72. The frame 108 can be constructed of a single piece or multiple pieces. In some instances, the frame 108 is electrically insulating. Suitable materials for the frame 108 include, but are not limited to, Teflon, Plexiglass, Kel-F, and PEEK. The fame includes a coupling portion 110 that is received within the base 70. The coupling portion 110 can include one or more sealing mechanisms 80 that provide a seal between the coupling portion 110 and the base 70. For instance, FIG. 2A and FIG. 2C illustrate o-rings that surround the coupling portion 110 such that the o-rings are positioned between the housing 10 and the base 70 upon construction of the cell. Other examples of suitable sealing mechanisms 80 include, but are not limited to, Silicone o-rings, Teflon coated Silicone o-rings, and Viton o-rings.

The frame 108 includes a frame attachment member 112 configured to be coupled with and/or attached to a secondary attachment member 114. In some instances, the frame attachment member 112 extends from a side of the frame as shown in FIG. 2C. A component passage 116 extends into or through the frame 108 and through the frame attachment member 112. The component passage 116 is formed such that a component such as a reference electrode 14 can extend through the frame 108.

The component extends through an opening in a sealing mechanism 118. The secondary attachment member 114 and frame attachment member 112 can be coupled such that the sealing mechanism 118 forms a seal between the component and the frame 108. For instance, the frame attachment member 112 can include threads that extend around the outside of the frame attachment member 112. The interior of the secondary attachment member 114 can also include threads that are complementary to the threads on the frame attachment member 112. As a result, the secondary attachment member 114 can be threaded and/or screwed onto the frame attachment member 112 with the sealing mechanism 118 between the frame attachment member 112 and the secondary attachment member 114. The threading of the secondary attachment member 114 onto the frame attachment member 112 can continue until the sealing mechanism 118 is compressed. The compression can form the seal between the sealing mechanism 118 and the component and also between the sealing mechanism 118 and the frame attachment member 112. Examples of suitable sealing mechanisms 118 include, but are not limited to, gaskets, ferrules, o-rings, and attachment with adhesives such as glues and epoxies. In some instances, a seal between the component and the sealing mechanism 118 can be formed using other mechanism such as the placement of a glue, adhesive, epoxy, and/or sealant between the component and the sealing mechanism 118. Additionally or alternatively, a seal between the component and the frame attachment member 112 can be formed using other mechanism such as the placement of a glue, adhesive, epoxy, and/or sealant between the component and the sealing mechanism 118. These other mechanisms for forming seals can be used in addition to, or as an alternative to, the compression of the sealing mechanism 118 provided by the coupling of the frame attachment member 112 and the secondary attachment member 114.

Although FIG. 2C discusses one or more mechanisms for forming a gas-tight seal between the frame 108 and a counter electrode 14, one or more of these mechanism can be employed to form a gas-tight seal between other components and the housing 10. For instance, one or more of these mechanisms can be employed to form a gas-tight seal between a material conduit 12, a reference electrode 16, or a counter electrode 16 and the sub-reservoir cover 72 or the assembly cover 74. As an example, the counter electrode 14 illustrated in FIG. 2C can be replaced with a material conduit 12 or another electrode such as a reference electrode 16 and the sub-reservoir cover 72 of FIG. 2C can be the sub-reservoir cover 72 or another part of the housing 10 such as the assembly cover 74. Accordingly, the seal between housing 10 and the material conduits 12, the counter electrode, and the reference electrode of FIG. 1A can be constructed according to FIG. 2C and/or the associated text.

The cell of FIG. 1A through FIG. 1E is disclosed as having multiple sets of brushes 46 where each set is associated with a different electrode in the assembly 20. However, as is evident from FIG. 2B, the assembly 20 may include a single electrode. As a result, the cell can include a single set of brushes 46 as is evident from FIG. 2A and FIG. 2B. Further, each set of brushes 46 is disclosed as having multiple brushes 46. Increasing the number of brushes 46 in electrical communication with an electrode can help maintain the electrical communication between the electronics and the electrodes during rotation of the assembly 20. However, in some instances, a single brush 46 in electrical communication with an electrode is desirable. As a result, one or more sets of brushes 46 can include a single brush 46. Accordingly, the cell can include as few as one brush 46.

Although the above illustrations show the working electrode 22 and the follower shaft 36 as different pieces, the working electrode 22 and follower shaft 36 can have a one-piece construction. Additionally or alternately, the ring electrode 60 and ring conductor 62 can have a one-piece construction.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A rotating disk electrode cell, comprising:
a housing that includes a reservoir for receiving a sample for an electrochemical experiment,
a shaft positioned within the housing so as to rotate around a longitudinal axis of the shaft, the shaft having a first end and a second end,
the first end of the shaft and the second end of the shaft being positioned inside of the housing and the shaft does not extend outside the housing,
a working electrode fixed to the first end of the shaft, and
a reference electrode located within the housing to contact the sample and offset from the longitudinal axis of the shaft,
wherein the shaft is magnetically coupled to a drive shaft across the housing.

2. The cell of claim 1, further comprising:
a shroud positioned over a lateral side and an upper surface of the working electrode and over a portion of the shaft, the shroud forming a functional surface extending beyond the lateral side of the working electrode, the diameter of the functional surface being configured to provide a predetermined diffusion layer over the working electrode during operation of the rotating disk electrode cell.

3. The cell of claim 2, wherein the shroud is electrically insulating.

4. The cell of claim 2, wherein the shroud includes material selected from the group consisting of Teflon, polyetheretherketone (PEEK), and polyetheretherketone (Kel-F).

5. The cell of claim 1, wherein the second end of the shaft is located between the housing and first end of the shaft.

6. The cell of claim 1, wherein one or more brushes are in electrical communication with the shaft and are positioned inside of the housing.

7. The cell of claim 1, further comprising:
an electrically-insulating shroud entirely encasing a lateral side and an upper surface of the working electrode and a portion of the shaft, the shroud extending beyond the lateral side of the working electrode.

8. A rotating disk electrode cell, comprising:
a reservoir cover that holds a shaft such that the shaft can rotate around a longitudinal axis of the shaft without the shaft extending through the reservoir cover;

a housing, detachably attached to the reservoir cover, that includes a reservoir for receiving a sample for an electrochemical experiment, the shaft being positioned within the housing so as to rotate around the longitudinal axis of the shaft, the shaft having a first end and a second end, the first end of the shaft and the second end of the shaft being positioned inside of the housing so that the shaft does not extend outside the housing;

a working electrode fixed to the first end of the shaft, and a reference electrode located within the housing to contact the sample and offset from the longitudinal axis of the shaft.

9. The cell of claim 8, wherein the second end of the shaft is located between the cover and the first end of the shaft.

10. The cell of claim 8, wherein the cover extends over the second end of the shaft.

11. The cell of claim 8, wherein the shaft is magnetically coupled with a drive shaft across the cover.

12. The cell of claim 8, wherein one or more brushes are in electrical communication with the shaft and are positioned inside of the cover.

13. The cell of claim 8, further comprising:

an electrically-insulating shroud positioned over a lateral side and an upper surface of the working electrode and over a portion of the shaft, wherein the shroud includes material selected from the group consisting of Teflon, polyetheretherketone (PEEK), and polyetheretherketone (Kel-F).

14. A rotating disk electrode cell, comprising:

a housing that includes a reservoir for receiving a sample for an electrochemical experiment, a shaft positioned within the housing so as to rotate around a longitudinal axis of the shaft, wherein the shaft does not extend outside the housing and wherein the shaft is magnetically coupled to a drive shaft across the housing, a working electrode fixed to an end of the shaft, a reference electrode located within the housing to contact the sample and offset from the longitudinal axis of the shaft, and one or more brushes that make electrical contact with the shaft and are positioned inside of the housing.

15. The cell of claim 14, wherein the one or more brushes are each a carbon brush.

16. The cell of claim 14, wherein at least one of the one or more brushes is in electrical communication with the working electrode.

17. The cell of claim 5, wherein the housing extends over the second end of the shaft.

18. A rotating disk electrode cell, comprising:

a reservoir cover that holds a shaft such that the shaft can rotate around a longitudinal axis of the shaft, wherein the shaft does not extend through the reservoir cover and wherein the shaft is magnetically coupled to a drive shaft across the reservoir cover;

a working electrode fixed to an end of the shaft;

a reference electrode mounted on reservoir cover and offset from the longitudinal axis of the shaft; and one or more brushes that make electrical contact with the shaft and are positioned inside of the reservoir cover.

19. The cell of claim 18, wherein the one or more brushes are each a carbon brush.

20. The cell of claim 18, wherein at least one of the one or more brushes is in electrical communication with the working electrode.

* * * * *